United States Patent
Gahlings et al.

(10) Patent No.: US 11,674,921 B2
(45) Date of Patent: *Jun. 13, 2023

(54) ONLINE REFERENCE CALIBRATION

(71) Applicant: ANB Sensors Ltd, Cambridge (GB)

(72) Inventors: Steven A. Gahlings, Cambridge (GB); Nathan Lawrence, Hail Weston (GB); Kay Louise McGuinness, Harston (GB)

(73) Assignee: ANB Sensors Ltd, Cambridgeshire (GB)

(*) Notice: Subject to any disclaimer, the term of this patent is extended or adjusted under 35 U.S.C. 154(b) by 430 days.

This patent is subject to a terminal disclaimer.

(21) Appl. No.: 16/755,516

(22) PCT Filed: Oct. 11, 2018

(86) PCT No.: PCT/EP2018/077797
§ 371 (c)(1),
(2) Date: Apr. 10, 2020

(87) PCT Pub. No.: WO2019/073002
PCT Pub. Date: Apr. 18, 2019

(65) Prior Publication Data
US 2020/0264131 A1    Aug. 20, 2020

(30) Foreign Application Priority Data

Oct. 11, 2017 (GB) .................................. 1716652
Oct. 11, 2017 (GB) .................................. 1716660
Feb. 12, 2018 (WO) ................. PCT/EP2018/000097

(51) Int. Cl.
*G01N 27/416* (2006.01)
*G01N 27/30* (2006.01)
(Continued)

(52) U.S. Cl.
CPC ......... *G01N 27/301* (2013.01); *G01N 27/302* (2013.01); *G01N 27/308* (2013.01);
(Continued)

(58) Field of Classification Search
CPC ............... G01N 27/301; G01N 27/414; G01N 27/4165; G01N 27/4167; G01N 27/48; G01N 33/18
See application file for complete search history.

(56) References Cited

U.S. PATENT DOCUMENTS 4,686,011 A    8/1987  Jaeckle
5,382,331 A *  1/1995  Banks .................... G01N 27/38
                                                        204/402
(Continued)

FOREIGN PATENT DOCUMENTS

GB          2559619 A      8/2018
WO    WO 2010111531 A2 *  9/2010  ............. G01N 27/30
WO       2016069935 A1    5/2016

OTHER PUBLICATIONS

International Search Report and Written Opinion for International Application No. PCT/EP2018/077797, dated Dec. 21, 2018. (10 pages).
Office Action for EP Patent Application 18786743.7 dated Sep. 16, 2021, 5 pages.

*Primary Examiner* — Alexander S Noguerola
(74) *Attorney, Agent, or Firm* — Mughal IP P.C.

(57) ABSTRACT

An online calibration system for an electrochemical sensor. The calibration system comprises a calibration electrode coupled with a redox species, where the redox species is configured to control a pH of a reference solution local to the calibration electrode, such that when a voltammetric signal is applied to the calibration electrode the output generated from the calibration system is determined by the local environment pH. The output signal from the calibration system is used to calibrate a reference potential generated by (Continued)

a reference system of the electrochemical sensor to correct for drift in the reference potential when the electrochemical sensor is being used. The calibration electrode may be disposed in a reference cell of the electrochemical sensor.

43 Claims, 11 Drawing Sheets

(51) Int. Cl.
*G01N 27/333* (2006.01)
*G01N 27/36* (2006.01)
*G01N 27/403* (2006.01)
*G01N 27/48* (2006.01)
*G01N 33/18* (2006.01)

(52) U.S. Cl.
CPC ........... *G01N 27/333* (2013.01); *G01N 27/36* (2013.01); *G01N 27/4035* (2013.01); *G01N 27/4163* (2013.01); *G01N 27/4165* (2013.01); *G01N 27/4167* (2013.01); *G01N 27/48* (2013.01); *G01N 33/18* (2013.01)

(56) References Cited

U.S. PATENT DOCUMENTS

| | | |
|---|---|---|
| 11,307,168 B2 * | 4/2022 | Gahlings ............ G01N 27/3277 |
| 2014/0332411 A1 | 11/2014 | Lawrence |
| 2015/0027887 A1 | 1/2015 | Lee |

* cited by examiner

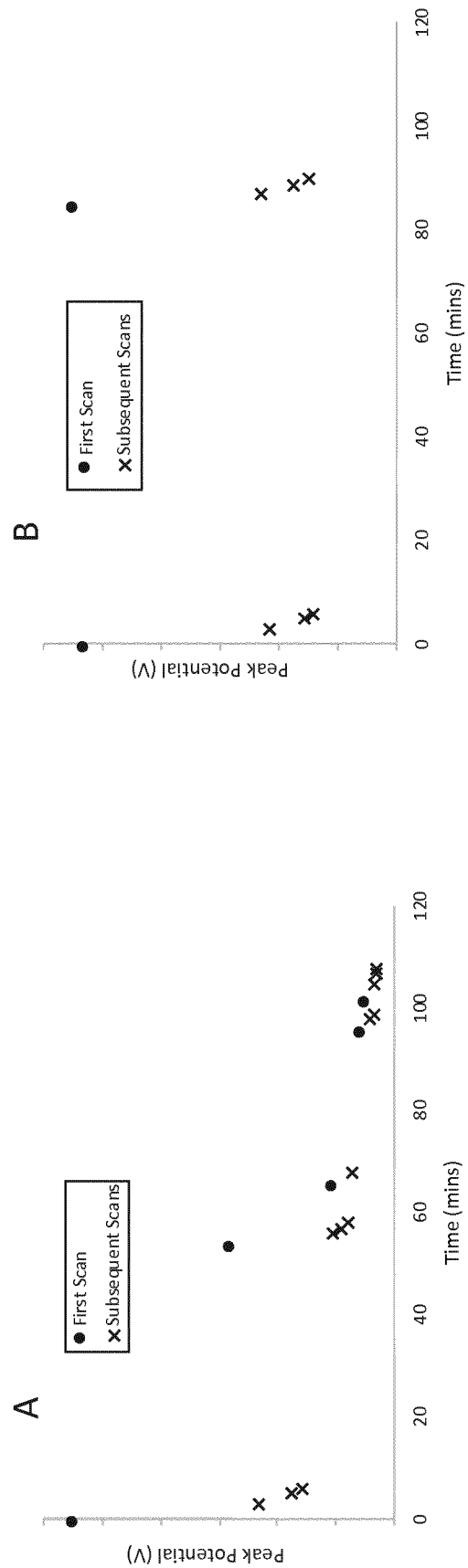

ONLINE REFERENCE CALIBRATION

This application is a U.S. National Stage of International Application No. PCT/EP2018/077797, filed Oct. 11, 2018, which claims the benefit of Great Britain Patent Application No. 1716652.1 filed on Oct. 11, 2017, Great Britain Patent Application No. 1716660.4 filed on Oct. 11, 2017, and International Application No. PCT/IB2018/000097, filed Feb. 12, 2018; the entire disclosures of all are hereby incorporated by reference in their entireties into the present disclosure for all purposes.

BACKGROUND

The present disclosure describes an online calibration system for an electrochemical sensor. The online calibration system comprises a calibration electrode configured to be deployed in a reference cell of the electrochemical sensor and to contact a reference solution therein. The calibration electrode comprises a redox species that is sensitive to pH/hydrogen ion concentration and is configured to set a pH of the reference solution local to the calibration electrode, such that when an electrochemical/voltammetric signal is applied to the calibration electrode, the calibration electrode generates an electrochemical/voltammetric response that has a constant feature, such as a peak potential, corresponding to the set pH of the reference solution local to the calibration electrode. The reference potential of the electrochemical sensor produced by the reference cell is calibrated by comparing a difference between the constant feature of the electrochemical/voltammetric response of the calibration electrode and the reference potential while the electrochemical sensor is deployed and/or being used. By repeatedly processing this difference, the reference potential can be calibrated online, without manual intervention.

In general there are three types of electrochemical sensors, voltammetric sensors, potentiometric sensors and/or amperometric sensors.

Amperometric sensors normally comprise at least a first electrode and a reference electrode. In use, a voltage is applied between the first electrode and the reference electrode and the resulting current between the first electrode and the reference electrode is measured. The current is produced by oxidation/reduction of a chemical species that the sensor is configured to detect and the measured current is indicative of the concentration of the chemical species.

For the measured current to be meaningful, the potential applied between the first electrode and the reference electrode needs to be a known potential. In many amperometric sensors, the reference electrode is contacted with a reference solution, which is a solution containing chloride ions, such as potassium chloride (KCl) solution, a sodium chloride (NaCl) solution and/or the like, to maintain the potential of the reference electrode as a constant. However, in use, the reference solution may become diluted, reducing the concentration of Cl ions, contaminated and, as a result, the potential applied between the first electrode and the reference electrode may drift, reducing the accuracy of the reference system.

Voltammetric/potentiometric sensors are some of the most common types of electrochemical sensor. Potentiometric sensors are the basis for glass electrodes (used for measuring pH, sodium (Na+), potassium (K+), lithium (Li+) and the like), solid membrane electrodes (based on the chemical process AgX for X−), liquid membrane electrodes (e.g. containing a ligand for M+ complexation and used in calcium (Ca+) and K+ sensors), pH-meter-based gas detectors (e.g. carbon dioxide ($CO_2$) sensors, ammonia ($NH_3$) sensors etc.) and some solid oxide sensors (e.g. zirconia-based oxygen ($O_2$) sensors). Voltammetric sensors may be used to measure pH, glucose, oxygen, hydrogen sulphide, for biosensing, for pharmaceutical sensing and/or the like. Potentiometric/voltammetric sensors measure a potential difference between an electrode or environment that is sensitive to the desired analyte and an electrode or environment that is insensitive to the analyte. In such sensors, an electrode or environment that is sensitive to the analyte is known as the sensing electrode and the electrode or environment that is insensitive to the analyte is known as the reference electrode.

Ion-sensitive field-effect transistors (ISFETs) are a new generation of solid state potentiometric sensor. In an ISFET, the sensing electrode is replaced with ion selective field effect transmitter, which measures a voltage between a source and a drain that is dependent on a concentration of an analyte in a solution being measured. To process properties of an analyte this source-drain voltage is measured against an output from a reference electrode housed in a well-defined environment.

For both traditional potentiometric and ISFET sensors, significant work has been performed to developing novel sensing electrode to measure different analytes/ions and/or to improve the accuracy/sensitivity for sensing of an ion/analyte. This work has resulted in the development of a range of commercial sensors that can achieve the desired selectivity and sensitivity to measure a range of analytes/ions.

However, despite the abundance and importance of potentiometric and ISFET sensors, operation of the sensors is problematic due to instabilities in the reference electrode. Typically, the reference electrode comprises a silver/silver chloride (Ag/AgCl) electrode that is held within a defined environment, containing a reference solution, behind a porous frit that allows for electrical conductivity to the solution that the sensor is measuring.

For a typical silver-silver chloride (Ag/AgCl) reference system, the Ag/AgCl electrode is stored in a solution with known properties when not in operation as the electrode can dry out when held in a dry atmosphere. Also, the Ag/AgCl sensor requires periodic recalibration due to drifts in the reference electrode potential because the chemistry of the electrode may change and/or ions may pass through the frit and perturb the environment. Furthermore, potentiometric systems typically operate in a continuous single point measurement mode, which is a mode where a known current is held between the reference and sensing electrode (typically 0) and the potential difference is constantly measured.

The very nature of this measurement means that any drift in the reference electrode during use is difficult to monitor, as there is no way to detect the drift and as a result the drift may be wrongly assigned to variations in the analyte concentration; typically corrections for drift are made after use when the sensor is recalibrated and any changes in the calibration shown before and after use are extrapolated linearly and the data from the sensor is revised in accordance with the extrapolations. However, such assumptions mean that the sensor may provide inaccurate results and sensor operation requires manual input. For example, for regulatory purposes it is necessary to be able to calibrate sensors requiring use of a standard extrapolation process to ensure for standardized measurements. More importantly, the calibration requirement means that the sensors require constant calibration, which may be expensive and or require user intervention, meaning the sensor cannot be accurately used in an online process and/or autonomously.

Several researchers have taken on the challenge of increasing the stability of the reference electrode and numerous methods have been proposed to overcome the issue.

U.S. Pat. No. 5,419,826 describes an ion-selective reference probe adapted for use with potentiometric measurement systems. The reference probe is non-chloride based and employs a specially adapted electrolyte, which is reversible with regard to ionic activity.

United States Patent Publication Number 20030024812 discloses a solid state electrochemical reference system, containing two or more electrodes, wherein the half-cell potential of at least one electrode is determined by the concentration of a specific ion anticipated to be present in all test solutions. The ion concentration measured in the cell by a first electroanalytical technique does not depend on a known reference electrode potential, such that said electrode, its half-cell potential being calculable from the measured ion concentration, can serve as a reference electrode in one or more subsequent electroanalytical techniques that do depend on a known reference electrode potential, said subsequent technique or techniques being carried out in the same cell.

U.S. Pat. No. 6,398,931 details an improved combination ion-selective electrode apparatus comprising an electrode body, a reference electrode, and an ion-sensing electrode. The reference electrode comprises an ion-permeable junction and a removable membrane cap contains an ion-selective membrane. The membrane cap can be removed from the ion-selective electrode apparatus without endangering the integrity of the reference electrode and is distinct from the ion-permeable junction.

European Patent Number 2 932 249 describes a reference electrode for an electrochemical sensor that comprises an inner reference element, where inner reference element has been embedded into a solid electrochemically active composite material.

U.S. Pat. No. 7,462,267 describes a reference electrode consisting of a metal in contact with an electrolyte containing an anion or cation whose concentration in part determines the redox potential of the electrode. This electrolyte contains a polyelectrolyte that partially and reversibly binds the chemical cation or anion thus lowering the free concentration of the cation or anion compared to the osmotic pressure of the same concentration of cation or anion if present as a simple salt. The polyelectrolyte can be anionic or cationic depending on the chemistry of the redox electrode and a thickener may also be added to the electrolyte.

However, to-date, the techniques for stabilizing/calibrating the reference electrode are complex, require manual intervention and regular maintenance, and use potentiometric operation, which may compound/mask stability errors. Because of the need to recalibrate the reference system of most electrochemical sensors, the sensors cannot be accurately used for long duration operation, cannot be used in an autonomous/networked system, and require costly manual calibration.

SUMMARY

In embodiments of the present disclosure, a calibration system is provided that comprises a calibration electrode, which may comprise a working electrode, that is used to make a voltammetric/electrochemical measurement and this measurement is used to verify/calibrate the electrochemical potential of a reference electrode of a potentiometric sensor. In this way, the calibration system can provide a correction to any drift in the reference electrode, without manual intervention. Moreover, with respect to ion selective sensors and/or amperometric sensors, because the calibration measurement is an electrochemical/voltammetric measurement the drift is not masked by, and/or is independent of potentiometric operation of the electrochemical sensor.

For purposes of this disclosure, the term electrochemical and voltammetric are used interchangeably with respect to applying a potential to a redox species. For example, in embodiments of the present disclosure, a potential is swept across the calibration electrode and this swept potential may be referred to as a voltammetric or electrochemical signal or as a voltammetric or electrochemical sweep. The term 'voltammetric' is commonly used to a potential sweep and the term 'electrochemical' is used to refer to a potential applied to a chemical species and/or the resulting electrical signal generated by the application of the potential since it is an electrochemical process.

For purposes of this disclosure, the calibration electrode is configured to be a working electrode in an electrochemical cell.

For purposes of this disclosure, the other electrodes in the electrochemical cell with the calibration electrode may be referred to as counter electrodes, reference electrodes and/or auxiliary electrodes.

In embodiments of the present disclosure, the calibration electrode is used in an electrochemical/voltammetric system, which may comprise a counter and a reference/auxiliary electrode, to generate a voltammetric response. The electrochemical/voltammetric response of the calibration electrode is used to calibrate a reference system of the electrochemical sensor that generates a reference potential, where the reference potential is produced by a reference system comprising a reference cell.

In embodiments of the present disclosure, the calibration electrode comprises a redox active species (a species that undergoes oxidation/reduction when a current/potential is applied) that is sensitive to pH (the oxidation/reduction current changing with respect to pH/hydrogen ion concentration) and configured to control the pH of a reference solution local to the calibration electrode. The redox active species may control the pH of the local environment proximal to the calibration electrode in the following ways. First, the redox active species may comprise either an acid or a base and/or contain acid or base moieties. In this way, the acidic or basic nature of the redox active species sets the pH of the local environment of the reference because the reference solution, having a low buffering capacity, cannot buffer the effect of the acidic or basic redox active species. In the second case, the redox active species may trigger the pH of the local environment of the reference solution by consuming or donating protons to the reference solution when a potential is applied to the redox active species. Again, because the reference solution cannot buffer the effect of the proton consumption or donation, the redox active species sets the local pH of the reference solution proximal to the calibration electrode.

The reference solution is the solution contained in a reference chamber of the electrochemical sensor, and as described above, normally comprises potassium chloride solution or the like. The reference solution provides a saturated chloride ion solution to maintain a constant reference potential. Potassium chloride, sodium chloride and the like are bufferless, low buffering capacity solutions. Because these reference solutions have a low buffering capacity or contain no buffer, the redox species will affect the local environment of the reference solution proximal to the redox species as there is no buffer/buffering capacity to buffer the local effect of the redox species. In embodiments of the present disclosure, redox active species sensitive to pH may comprise: a chemistry that affects hydrogen ion concentration (consumes or produces protons during oxidation/reduction), a base, an acid, base moieties, acid moieties or the like to set a local pH of the reference solution to a value greater or less than a pH of 7. By way of example, the redox species may comprise anthraquinone, ferrocene, salicylic acid or the like. In fact, all redox active systems that are sensitive to pH will set the local pH of a low buffering capacity solution during oxidation/reduction, and this effect can only be prevented by using a redox active system that essentially negates the effect. While embodiments of the present disclosure can use a redox species that sets the local pH of the reference solution to 7, this is not a preferred embodiment as it may complicate calibration processing.

In embodiments of the present disclosure, an electrochemical/voltammetric sweep is applied to the calibration (working) electrode to generate an electrochemical/voltammetric response from the calibration electrode, where the electrochemical/voltammetric response comprises oxidation/reduction of the redox active species. The voltammetric response includes singularities/peaks in the oxidation/reduction current and a potential corresponding to these peaks/singularities is known as the peak potential. The peak potential for redox active species sensitive to pH is set by the pH of the solution that the calibration electrode is contacting.

In embodiments of the present disclosure, the pH of the reference solution local to the calibration electrode is set by the redox active species. As such, the peak potential generated by the calibration electrode is a constant value. In operation, when an electrochemical/voltammetric sweep is applied to the redox active species, the redox active species undergoes oxidation/reduction. During this oxidation/reduction, the redox active species donates or consumes protons, depending upon the chemistry of the redox active species, and because the contacted solution has a low buffer capacity this effect is not buffered by the solution so the redox species produces an electrochemical/voltammetric response that is governed by the proton/hydrogen ion concentration proximal to the calibration electrode that is generated.

In embodiments of the present disclosure this constant peak potential, and/or a related potential in the electrochemical/voltammetric response, is used as a reference/calibration value to calibrate the reference potential of the electrochemical sensor. As such, in embodiments of the present disclosure, the calibration/working electrode may be swept periodically, while the electrochemical is deployed/in use and the determined peak potential used to calibrate the reference potential, without manual intervention.

In some embodiments, calibration of the reference electrode potential is provided by measuring a difference between the potential of the reference electrode and a peak potential or the like produced by the calibration electrode, where any changes in the difference are used to correct/calibrate the output from the sensor since the peak potential is a constant potential and any changes will be due to drift in the reference potential. Because the reference solution of most electrochemical sensors comprise chloride ions, the redox active species of the calibration electrode is selected such that it is insensitive to chloride ion concentration. In this way, the calibration electrode and the peak potential generated by the calibration electrode is independent of the concentration of chloride ions of the reference solution.

Surprisingly, applicant has found from extensive testing that the effect of the redox active species controlling the local pH of the reference solution, and the resulting constant peak potential generated by oxidation/reduction of the redox active species, is unperturbed by: large dilution of the reference solution (up to 50% dilution); presence of acids or bases in the reference solution; presence of active chemistries in the reference solution; presence of carbonates, e.g. hard water (carbonates are problematic as they affect the buffering capacity of the solution and thereby reduce the ability of the redox active species to set the local pH); and/or the like.

While peak potential, a peak in the electrochemical/voltammetric signal generated by the calibration electrode may be used to calibrate the reference potential, other potentials in the electrochemical/voltammetric response, such as a change in direction of the generated sweep signal, a maximum rate of change on the sweep signal or other characteristic that can be ascertained by signal processing—may be used to obtain a calibration potential of the calibration electrode and this may then be used to calibrate the reference electrode. In some embodiments, multiple points of the electrochemical/voltammetric sweep response of the calibration electrode may be analysed to generate a calibration potential. Moreover, since the pH set by the redox active species in a reference solution is known, can be calculated, or can be determined from tests/experiments, the signal processor can analyze the electrochemical/voltammetric response to an applied potential sweep using this knowledge.

Since the voltammetric/electrochemical measurement is not a potentiometric measurement, unlike the measurement from the reference electrode, the measurement provides a truly independent calibration. Moreover, the voltammetric/electrochemical measurement may be made periodically reducing issues/maintenance requirements associated with continuous/high frequency measurements. Also, the calibration system may be used with a robust reference system, such as an Ag/AgCl reference system and does not rely on potentiometrically measuring the presence of an ion.

In embodiments of the present disclosure, the calibration electrode comprises a redox active species that controls the local environment of a reference solution of the electrochemical sensor proximal to the electrode. This control of the local environment may in some embodiments be provided by contacting the electrode with a low buffer/low ionic strength solution, such as water, seawater, sodium chloride solution, silver, potassium chloride solution and/or the like. In such, an environment, the calibration electrode, because of the low buffer/ionic strength of the analyte, 'sees' an environment controlled by the redox active species itself. For example, a common redox active species for electrochemical sensors, anthraquinone will measure a pH of about 10 or 11 when a voltammetric signal is applied because the anthraquinone will consume protons during reduction triggering a change in pH in the local environment that is measured by the sensor. This effect of the redox species will occur for most redox active species, unless they are specially configured, when the analyte contacted with the redox species is a low buffer/low ionic strength analyte In other embodiments, a redox species containing acid groups, such as salicylic acid etc., or alkali groups, such as species containing amine groups, acid groups will create an acidic or alkaline local environment irrespective of the acidity/alkalinity of the fluid being sensed. In such embodiments, the local environment is controlled by the acidic/alkaline redox species even if the buffer/ionic strength of the analyte contacting the redox species is not low. In some embodiments of the present invention, redox species with acid or alkali groups are used to move the pH of the local environment away from a neutral reading, a pH of 7, to provide a known reference potential output from the calibration electrode when a voltammetric signal is applied to the calibration electrode.

Such an approach can be utilized in all electrochemical systems which require a stable reference electrode system. Potassium ion sensors utilize a valinomycin modified membrane to provide the ion-selective response, in conjunction with a standard Ag/AgCl electrode. The longevity of such systems is often compromised by instability in the reference electrode. In such systems the addition of a calibration sweep system using an electrode with a controlled environment would obviate the lifetime issues associated with the drift in the reference electrode.

Up until now, the effect of the redox species controlling the local environment has been identified as a weakness in electrochemical sensor operation as it produces incorrect output from the sensor since the sensor measures properties of the local environment, which is controlled by the redox species, not the properties of the solution being tested. However as described herein, the effect provides an electrode that has a known output, due to its control of the local environment, that may be used for calibration.

In sensors designed for use in low buffer/low ionic strength solutions, such as water/seawater or the like, the calibration electrode may be contacted directly with the low buffer/low ionic strength fluid and the redox species control the local environment to produce a known/stable potential output from the calibration electrode. In sensors that may be used with fluids with unknown properties and/or high ionic strength/buffer strength, the calibration electrode may be contacted with a known analyte, such as an analyte kept behind a frit or the like, for example an aqueous solution with low ionic/buffer strength. In some embodiments, the calibration electrode may be contacted with the same fluid environment as the reference electrode, i.e., a reference solution held in a reservoir behind a frit that allows for electrical/ion conductivity with the solution being tested/analyzed.

In some embodiments, the calibration system may comprise an additional electrochemical cell that is placed inside an existing reference electrode chamber. In such an arrangement, the reference electrode in the existing reference electrode chamber may be used as a reference electrode for the calibration system.

BRIEF DESCRIPTION OF THE DRAWINGS

In the figures, similar components and/or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

FIG. 8 details the plot of peak potential against time showing the peak potential measured for a first, 10th, 15th and 20th scan.

DESCRIPTION

Figure 1A:
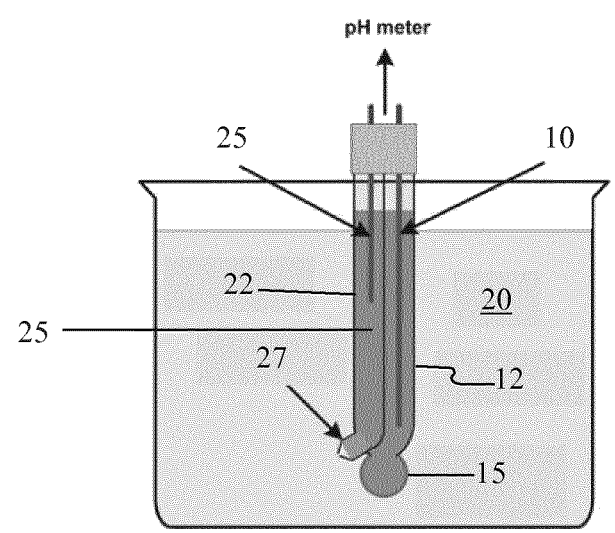
FIG. 1A illustrates a glass electrode pH sensor with a reference electrode.

The ensuing description provides some embodiment(s) of the invention, and is not intended to limit the scope, applicability or configuration of the invention or inventions. Various changes may be made in the function and arrangement of elements without departing from the scope of the invention as set forth herein. Some embodiments may be practiced without all the specific details. For example, circuits may be shown in block diagrams in order not to obscure the embodiments in unnecessary detail. In other instances, well-known circuits, processes, algorithms, structures and techniques may be shown without unnecessary detail in order to avoid obscuring the embodiments.

Some embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure and may start or end at any step or block. A process may correspond to a method, a function, a procedure, a subroutine, a subprogram, etc. When a process corresponds to a function, its termination corresponds to a return of the function to the calling function or the main function.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "computer-readable medium" includes, but is not limited to portable or fixed storage devices, optical storage devices, wireless channels and various other mediums capable of storing, containing or carrying instruction(s) and/or data.

Furthermore, embodiments may be implemented by hardware, software, firmware, middleware, microcode, hardware description languages or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class or any combination of instructions, data structures or program statements. A code segment may be coupled to another code segment or a hardware circuit by passing and/or receiving information, data, arguments, parameters or memory contents. Information, arguments, parameters, data, etc. may be passed, forwarded or transmitted via any suitable means including memory sharing, message passing, token passing, network transmission, etc.

Reference will now be made in detail to embodiments, examples of which are illustrated in the accompanying drawings and figures. In the following detailed description, numerous specific details are set forth in order to provide a thorough understanding of the subject matter herein. However, it will be apparent to one of ordinary skill in the art that the subject matter may be practiced without these specific details. In other instances, well known methods, procedures, components, and systems have not been described in detail so as not to unnecessarily obscure features of the embodiments. In the following description, it should be understood that features of one embodiment may be used in combination with features from another embodiment where the features of the different embodiment are not incompatible.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step. The first object or step, and the second object or step, are both objects or steps, respectively, but they are not to be considered the same object or step.

The terminology used in the description of the disclosure herein is for the purpose of describing particular embodiments only and is not intended to be limiting of the subject matter. As used in this description and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting", depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

For the purposes of this disclosure the following terms have the following meaning.

A "redox-species" is a compound or composition that may be oxidized and reduced. "Redox activity" refers to either or both of those processes.

A "redox sensitive species" is redox-species that is sensitive or substantially sensitive to the presence or concentration of an analyte in a sample within those user-defined application-specific tolerances. "Substantially sensitive" to an analyte is used to mean sensitive within the tolerances required for a given application, as those tolerances are defined by an end user.

A "redox-active material" is a compound or composition that may be oxidized and reduced. "Redox activity" refers to either or both of those processes.

A "reference electrode" (RE) is an electrode used to establish the potential difference applied to the working electrode (WE). Conventional REs have a certain fixed chemical composition and therefore a fixed electrochemical potential, thus allowing measurement of the potential difference applied to the WE in a known, controlled manner. An RE typically comprises two halves of a redox couple in contact with an electrolyte of fixed chemical composition and ionic strength. Because both halves of the redox couple are present and the composition of all the species involved is fixed, the system is maintained at equilibrium, and the potential drop (i.e., the measured voltage) across the electrode-electrolyte interface of the RE is then thermodynamically fixed and constant. For example a commonly used RE system is the Ag/AgCl/KCl system with a defined and constant concentration of KCl. The two half-cell reactions are therefore: $Ag++e-\rightarrow Ag$; and $AgCl+e-\rightarrow Ag+Cl-$. The overall cell reaction is therefore: $AgCl\rightarrow Ag++Cl-$ for which the Nernst equilibrium potential is given as: $E=E0-(RT/F)*\ln[Cl-]$, where E is the measured RE potential, E0 is the standard potential of the Ag/AgCl couple vs. the standard hydrogen electrode with all species at unit activity (by convention the standard hydrogen electrode is defined as having a potential of 0.0V); and R, T, and F are the universal gas constant, temperature, and Faraday constant, respectively, in appropriate units. Hence, the potential of this system depends only on the concentration (more strictly speaking the activity) of Cl— ion present, which, if this is fixed, provides a stable, fixed potential. Many other RE systems are known in the art. It is imperative that the composition of the RE remains constant, and hence almost no current should be passed through the RE (otherwise electrolysis will occur and the composition of the RE will change), which necessitates the use of a third electrode, the counter electrode (CE), to complete the circuit. However, two-electrode configurations can be used in the special case where the WE is a microelectrode, having at least one dimension typically smaller than 100 micrometers. In this case, the currents passed at the WE are small, and therefore a two-electrode cell can be used with a RE, but without the need for a CE.

A "sensor" is an electrode or collection of electrodes that generates a signal in response to the presence of an analyte. A sensor can include, for example, a working electrode, a counter-electrode and a reference electrode (either a conventional reference electrode or a pseudo reference electrode). A sensor can include, for example, a working electrode, a counter electrode and an analyte-insensitive electrode.

An "electrode" is a component of a sensor and may comprise a metal, carbon and/or the like. A variety of carbon substrates are suitable for use as substrate material in the electrodes of the present invention, including but not limited to carbon allotropes such as graphites, including pyrolytic graphite and isotropic graphite, amorphous carbon, carbon black, single- or multi-walled carbon nanotubes, graphene, glassy carbon, boron-doped diamond, pyrolyzed photoresist films, and others known in the art.

A "working electrode" is the electrode at which the electrochemical process for detecting the analyte of interest occurs. In a sensor, the working electrode may be sensitive to one or more analyte(s) in the test sample, or it may be chemically modified with analyte sensitive species/materials. The electrochemical response of the working electrode is measured after some perturbation to the system under study has been applied. For example, the perturbation may be the application of a potential difference to the working electrode that induces electron transfer to occur, and the resulting current at the working electrode is then recorded as a function of the applied potential (voltammetric mode). This example of mode of operation is illustrative and not exhaustive, as many other modes are known in the art. The working electrode may comprise a redox species that can undergo a reversible electrochemical redox reaction dependent upon the concentration of an analyte (hydrogen ions for a pH meter; other analytes for other analyte sensing devices) in a sample solution and an applied electrical potential. For example, where there is a high concentration of hydrogen ions present in a sample solution, the redox reaction occurs at a lower potential. Conversely, where there is a low concentration of hydrogen ions present in a sample solution, the redox reaction occurs at a higher potential. The relationship between these characteristic potentials and the sample solution pH is a function of the chemical identity of the redox species. An algorithm converts electrical potential to pH value to provide a means of determining the pH of an unknown sample.

FIG. 1A illustrates a glass electrode pH sensor. Glass electrodes are some of the most common electrochemical sensors. The glass electrode is an example of an ion selective electrode/sensor.

Glass electrode pH sensors are some of the most ubiquitous electrochemical sensors, since they use a well-established technology to measure a fundamental property, pH. The glass electrode comprises an internal electrode 10 contained in a measurement chamber 12. The glass electrode is disposed in a test solution 20 and the internal electrode 10 is in electrical communication with the test solution 20 via a glass membrane 15. The glass membrane 15 provides for ion exchange between a fluid in the measurement chamber 12 and the test solution 20.

As with most electrochemical sensors, the glass electrode includes a reference electrode 25. The reference electrode 25 is disposed within a reference chamber 22 that contains a reference solution 25. The reference solution 25 is configured to electrically communicate with the test solution 20 through a porous fit 27, which allows for equalization of electrical properties of the two solutions. By measuring a potential of the measurement electrode 10 with respect to a reference potential of the reference electrode 22 an output potential, which is set by the ion concentration of the test solution 20, can be communicated to the pH meter.

The glass electrode essentially consists of four major components, the glass membrane 15, the internal electrode 10, the reference electrode 25 and a glass stem. The internal electrode 10 and the reference electrode 25 are both disposed in solutions. In general, the solutions are the same solutions and may comprise solutions saturated with chloride ions, such as potassium chloride, sodium chloride etc. For best results, a symmetrical liquid cell is set up on both sides of the glass membrane. To set up the symmetrical cell, the internal fill solution in the glass and the reference fill solution are similar in their makeup. The symmetry is important so that the temperature curves for the two solutions are close, thereby canceling each other's temperature effect.

Reference electrodes work like a battery with the chemical components producing a predictable voltage that is also in electrical contact with the solution being measured. The reference output is a constant voltage thus, giving the glass a reference point to distinguish changes in hydrogen ion concentration seen as a potential across the glass membrane.

Figure 1B:
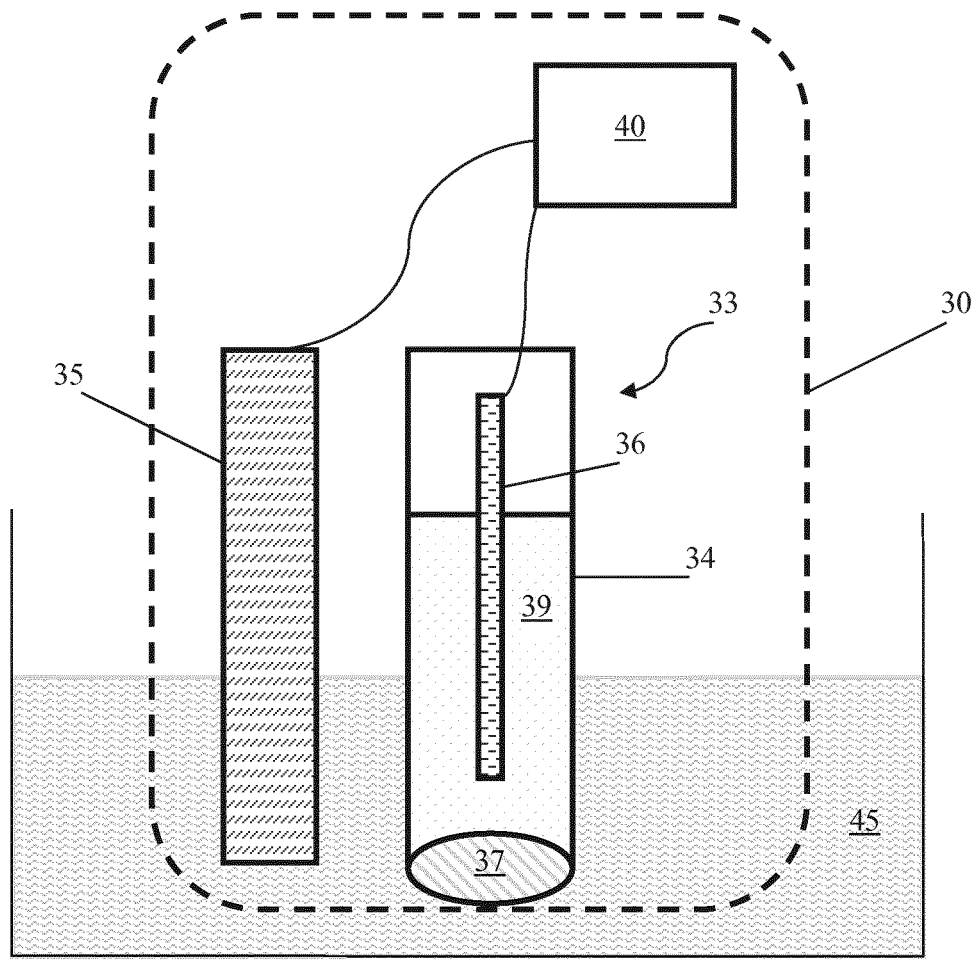
FIG. 1B is a schematic-type illustration of an electrochemical sensor comprising a reference electrode/reference system.

FIG. 1B is a schematic-type illustration of an electrochemical sensor.

In FIG. 1B, an electrochemical sensor 30 comprises a sensing system 35 and a reference system 33. The sensing system 35 may comprise a working electrode and be configured to contact a test solution 45. The sensing system 35 comprises a chemistry configured to undergo oxidation/reduction when an electrical signal is applied to the sensing system 35. The chemistry is selected such that the amplitude of the oxidation/reduction current and/or the potential associated with a peak of the oxidation/reduction current changes depending upon a concentration of a particular ion/chemical species that the electrochemical sensor is designed to detect/measure.

In the electrochemical sensor 30, the reaction from which concentration of an ion/chemistry of interest can be determined occurs at the surface of the working electrode 35 of the sensing system 35. In operation, the potential drop across the interface between the surface of the working electrode 35 and the test solution 45 (i.e., the interfacial potential) is controlled in the electrochemical sensor 30. However, it is impossible to control or measure this interfacial potential without placing another electrode, a counter electrode (not shown) in the test solution 45. By using the counter electrode and the working electrode 35, two interfacial potentials may be produced, neither of which can be measured independently. To be able to measure the interfacial potential of the working electrode 35, a requirement for the counter electrode is that its interfacial potential remains constant, so that any changes in the cell potential produce identical changes in the working electrode interfacial potential.

An electrode whose potential does not vary with current is referred to an ideal non-polarizable electrode, and is characterized by a vertical region on a current versus potential plot. However, there are no electrodes that behave in this ideal manner. As a result non-ideal behavior, the interfacial potential of the counter electrode in the two-electrode system discussed above varies as current is passed through the cell. This problem is overcome by using a three-electrode system, in which the function of the counter electrode is divided between a reference electrode 36 and one or more auxiliary electrodes (not shown). In this set-up, the potential between the working electrode 35 and the reference electrode 36 and the one or more auxiliary electrodes is controlled and current passes between the working electrode 35 and the one or more auxiliary electrodes. The current passing through the reference electrode 36 is reduced, as it is not desirable to have current flow through the reference electrode, by using a high-input-impedance operational amplifier as an input to reference electrode 36.

In the electrochemical sensor, the reference system 33 may comprise a reference chamber 34. The reference chamber 34 contains a reference solution 39 and the reference electrode 36. The reference electrode 36 is at least partially disposed within the reference solution 39. One of the most common reference systems is the silver-silver chloride reference system in which the reference electrode is formed from silver with a coating of silver chloride. The reference solution for the silver-silver chloride reference solution comprise a solution containing chloride ions, such as potassium chloride solution or sodium chloride solution.

The redox process equation for the silver-silver chloride reference system is:

AgCl+e-<=>Ag+Cl—

The reference solution 39 may comprise of the order of 3 Molar sodium chloride or potassium chloride.

The potential E for any electrode is determined by the Nernst equation, which relates E to the standard potential E0 and the activities of the redox components (the standard potential is the potential of the electrode at unit activity under standard conditions). The Nernst equation for the silver/silver chloride electrode is:

$$E = E^0 + \frac{RT}{nF} \ln \frac{1}{a_{Cl^-}}$$

It is generally more convenient to consider concentrations rather than activities. These parameters are related by the activity coefficient g:

$$a_{Cl^-} = \gamma_{Cl^-} [Cl^-]$$

The Nernst equation can therefore be rewritten as follows:

$$E = E^{0'} + \frac{RT}{nF} \ln \frac{1}{[Cl^-]}$$

Where E0' is the formal potential and is related to the standard potential by the equation:

$$E^{0'} = E^0 + \frac{RT}{nF} \ln \frac{1}{\gamma_{Cl^-}}$$

The standard redox potential (E0) for the silver/silver chloride redox reaction at 25 degrees Celsius is +0.222 V (vs. NHE), whereas the redox potential (E) for the BASi silver/silver chloride reference electrode at this temperature is +0.206 V (vs. NHE).

In the reference system 33, the reference chamber 39 includes a porous fit 37. The porous fit 37 ionicly conducting electrical pathway between the inside of the reference chamber 36 and the test solution 45. This is necessary in order to equalize the electrical conditions of the working electrode 35 and the reference electrode 36

However, Nernst equations for the silver-silver chloride reference system, show that variations in the chloride ion concentration in the reference chamber 34 alter the redox potential of the reference system 33. In operation of an electrochemical sensor, chloride ions may pass out of the reference chamber 34 through the porous fit 37 and/or the test solution 45 may pass through the porous fit 37 into the reference chamber 34. In both of these events, the chloride ion concentration in the reference chamber 34 is changed, and as a result the reference potential of the reference system 33 is changed. This change in reference potential is often referred to as drift. The result of reference electrode drift is inaccuracy in the measurement of the chemistry/ion of interest. To address reference electrode drift, the electrochemical sensor must be regularly recalibrated. Recalibration of the electrochemical sensor involves an operator of the electrochemical sensor measuring an output from the electrochemical sensor in at least three different solutions containing a known concentration of the ion/chemistry of interest so that the output from the electrochemical sensor can be compared to the known response that the sensor should have produced for the known concentrations and the sensor recalibrated to account for any difference found in the comparison.

By way of example, in the water industry, to meet regulations and manage the water resource multiple electrochemical pH sensors, commonly glass electrodes, are distributed through the water management infrastructure to monitor pH. To operate the pH sensors, engineers must periodically visit each of the electrochemical pH sensors and recalibrate the reference system. This is a time consuming and expensive necessity of operating existing electrochemical sensors. In the water industry, sensor manufacturers make sensors where recalibration may be performed every three months or so.

However, to obtain this extended recalibration duration, the senor accuracy is greatly diminished with resulting accuracy of the order of plus/minus twenty percent. The long duration is made possible by using software processing where an expected/interpolated drift may be programmed and the reference potential adjusted accordingly. However, monitoring actual operation of the reference system is not possible, and the accuracy of the measurements made between recalibrations, especially when the time between recalibrations is long, is questionable, leading many sensor operators to use more frequent recalibrations. Furthermore, electrochemical sensors used in more challenging industries than the water industry, such as in chemical processing and or chemical waste monitoring, operate in conditions where more reactive chemicals/ions may pass through the porous frit 37 into the reference chamber 34 affecting the reference potential generated by the reference system 33. Moreover, existing electrochemical sensors are in general "dumb" sensors that cannot provide quality assurance, quality control data regarding sensor operation. This need for frequent manual recalibration and/or dumb operation, mean that many electrochemical sensors, including the glass electrode, are not capable of networked operation.

Figure 2A:
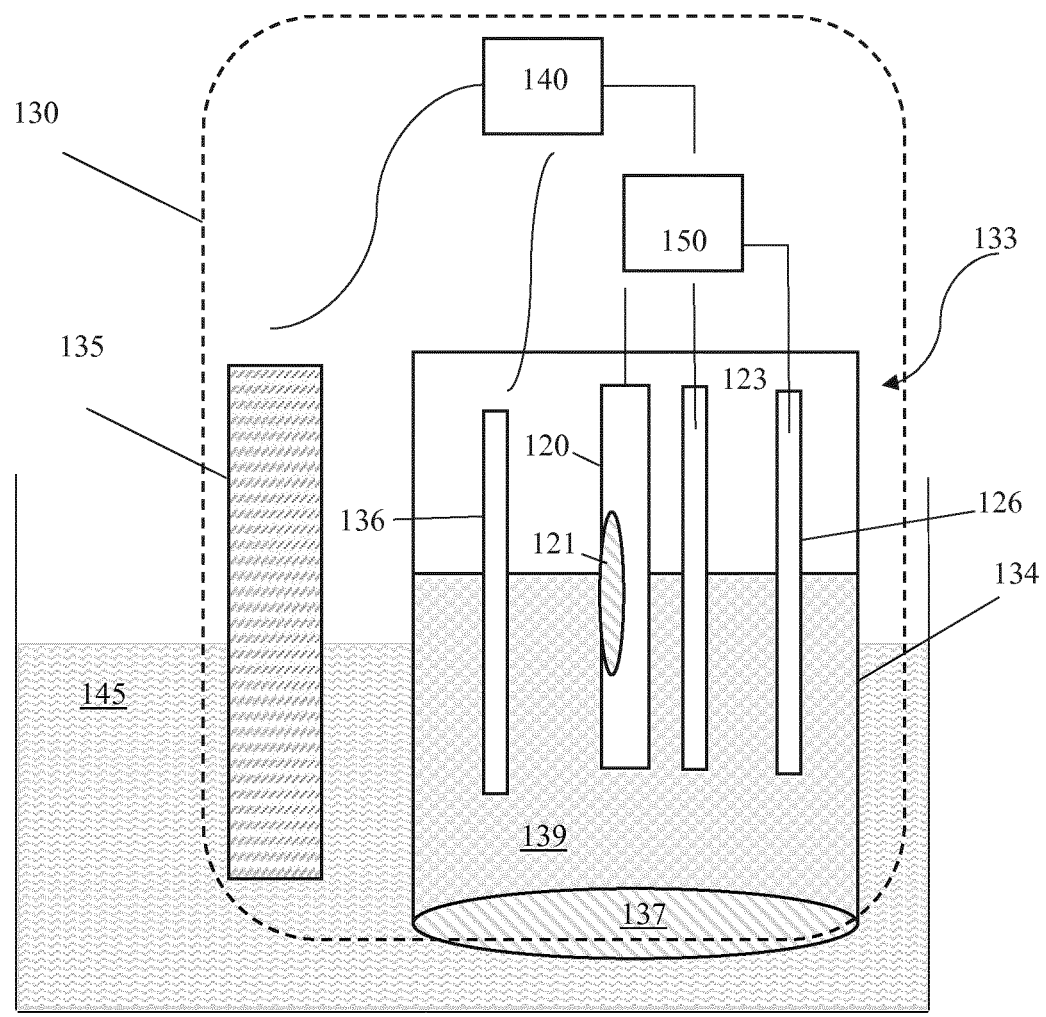
FIG. 2A illustrates an electrochemical sensor comprising a calibration system, in accordance with some embodiments of the present disclosure.

FIG. 2A illustrates an electrochemical sensor comprising an online calibration system, in accordance with some embodiments of the present disclosure.

As illustrated in FIG., 2A, an electrochemical sensor 130 comprises a sensing system 135 and a reference system 133. The sensor system 135 may comprise a sensing/working electrode and/or the like that is configured to provide an electronic response to an applied electronic signal that is dependent upon a concentration of an ion/chemical species in a test solution 145. The electrochemical sensor 130 may be an ion selective electrode, such as for example a glass electrode, an amperometric sensor, a redox sensor, an ISFET and/or the like.

A processor 140, comprising processing circuitry, is configured to communicate with the sensing system 135 to apply a signal to the sensing system 135 and to process the response of the sensing system 136 to the applied signal. To process the response of the sensing system 135, as explained with respect to FIGS. 1A and 1B, it is necessary to provide a reference potential to the processor 140 of the electrochemical sensor.

As depicted in FIG. 2A, the reference system 133 comprises a reference chamber 134. The reference chamber 134 contains a reference solution 139 and a reference electrode 136. The reference electrode 136 and the reference solution 139 are configured such that the reference electrode 136 generates a constant reference potential when a reference signal is applied to the reference electrode 136. For example, the reference electrode 136 may comprise a silver-silver chloride electrode and the reference solution 139 may comprise a solution containing chloride ions, such as sodium chloride solution, a potassium chloride solution or the like. In some embodiment, the reference solution 139 may comprise a paste, gel and/or the like.

In some embodiments of the present disclosure, a calibration system comprising a three-electrode system is provided in the reference chamber 134. As depicted, the three-electrode system comprising a working electrode 120, counter electrode 123 and a reference electrode 126. In some embodiments, the calibration system may comprise a single working electrode, a two-electrode system or a system comprising four or more electrodes. In some embodiments of the present disclosure, the one of the electrodes of the calibration system may comprise the reference electrode 136.

In embodiments of the present disclosure, the working electrode 120 comprises a redox species 121. The redox species 121 is configured to be sensitive to pH, i.e., the redox species is configured to generate a response signal to an applied electrical signal that varies depending upon a pH of a solution contacted by the working electrode 120. In embodiments of the present disclosure, the redox species 121 is configured to set the pH of a local environment of the reference solution 139 in which the working electrode 120 is disposed and to sense this set pH when a calibration signal is applied to the calibration system.

Suitable redox species that are sensitive to pH/hydrogen ion concentration and that will set the pH of the reference solution local to the calibration electrode may include, for example and without limitation: anthraquinone (AQ), phenanthrenequinone (PAQ), N,N'-diphenyl-p-phenylenediamine (DPPD), anthracene, naphthaquinone, para-benzoquinone, diazo-containing compounds, porphyrins, nicotinamides, including NADH, NAD+ and N-methylnicotinamide, quinone thiol, monoquaternized N-alkyl-4,4'-bipyridinium, RuO, and Ni(OH)2, ferrocene carboxylate, and derivatives of those compounds; CO-sensitive ASMs: ferrocenyl ferraazetine disulfide; iron porphyrins; alkaline metal cation sensitive ASMs: 1,1'-(1,4,10,13-tetraoxa-7,1-diazacyclooctadecane-7,16-diyl dimethyl), ferrocenyl thiol, other ferrocene derivatives containing covalently attached cryptands, and certain metal complexes with $Fe^{2+}/Fe^{3+}$, $Co^{2+}/Co^{3+}$, $Cu^+/Cu^{2+}$, ferrocenyl ferraazetine and ferrocenyl cryptands, substituted anthraquinones, mono-, di-, or poly-hydroxyl substituted AQ; mono-, di-, or poly-amino substituted AQ, ethyleneglycol or polyethyleneglycol-modified AQ, and/or the like. The person of skill in the art will appreciate that any redox species sensitive to pH, unless it has been specially configured will set the local pH of the reference solution when the redox species is oxidized/reduced because of the low buffering capacity of the reference solution.

As previously described, a problem with electrochemical pH sensors using a working electrode comprising a redox active species sensitive to pH is that when contacted with a low buffering capacity/bufferless solution, the redox active species sets the pH of the local environment of the low buffering capacity/bufferless solution proximal to the working electrode. In essence, because the solution has a low buffering capacity and/or contains no buffer, it cannot buffer the local effect of the redox active species on the solution. This results in a region close to the redox active species having a proton pH that is dependent upon the properties of the redox species. This problem has been identified as a limitation of the use of electrochemical sensors using redox active species to measure pH in low buffering capacity, bufferless solutions, such as water, seawater, sodium chloride solutions, potassium chloride solutions and/or the like. To overcome this problem, specialized redox chemistries have been developed that provide for accelerated response so that the redox chemistry is sensitive to the pH of the contacted solution not the pH of the local environment set by the redox species.

In embodiments of the present disclosure, the redox species 121 may comprise any redox species sensitive to pH that is not configured to overcome the effect of localized pH setting in low buffering capacity/bufferless solution. In preferred embodiments, the redox species 121 is selected to set a pH of the local environment of the reference solution 139 to a pH value that is greater than one pH unit above or below pH 7. Applicant has found that calibration processing is optimized when the redox active species 121 sets a pH that is not at or close to pH 7. In some embodiments, the redox active species 121 may comprise an acid, a base, acid moieties or base moieties.

Applicant has found that nearly all of the generally used redox species sensitive to pH can be used to set the pH of the local environment and to produce a response to this set pH, as very few of the redox active species sensitive to pH provide for overcoming the low buffer capacity issue. By way of example, Applicant has found that anthraquinone and its derivatives, some of the most commonly used redox species sensitive to pH, can be used as the redox active species 121. By way of example, anthraquinone sets the pH of the local environment of the reference solution to a pH value of about 10.

For embodiments of the present disclosure, the redox species 121 is configured to be sensitive to pH and to set a local pH of the reference solution 139 proximal to the working electrode 120. These features of the redox species 121 and the fact that the redox species 121 is not sensitive to chloride ion concentration, provide that a response of the redox species will be a constant value whatever the changes to the chloride concentration.

In embodiments of the present disclosure, the reference solution 139 comprises a low buffering capacity/bufferless solution. As noted above, the most common reference solutions for the reference system 133 comprise sodium chloride, potassium chloride, or the like. Both potassium chloride and sodium chloride solutions comprise low buffering capacity/bufferless solutions. Potassium chloride (KCl) reference solutions do not comprise any buffer in the reference solution, so are well suited to use in embodiments of the present disclsoure.

In some embodiments of the present disclosure, a calibration processor 150 may apply an electrochemical/voltammetric signal to the working electrode 120. The voltammetric signal may comprise a varying electronic signal, such as a square wave voltammetric signal, a ramped voltammetric signal and/or the like. In embodiments of the present disclosure, in which the calibration system comprises a three-electrode system, the voltammetric signal may be swept across between the working electrode 120, the counter electrode 123 and the reference electrode 126.

In response to the application of the voltammetric signal, the working electrode generates an electrochemical/voltammetric response. This response is dependent upon the oxidation/reduction current produce by the redox species 121. Since the redox species 121 is sensitive to pH, the oxidation/reduction current produced by the redox species 121 will depend upon the pH of the reference solution 139. In embodiments of the present disclosure, because the redox species 121 is configured to set the pH of the reference solution proximal to the working electrode 120/redox species 121, the voltammetric response will have constant features, e.g., a peak potential corresponding to a peak/singularity in the oxidation/reduction current, corresponding to the set pH. In embodiments of the present disclosure, the voltammetric response may be processed by the calibration processor into a voltammogram and/or into a representation showing working electrode potential versus redox current.

In embodiments of the present disclosure, the redox species 121 and the reference solution 139 are selected so that the redox species 121, which is sensitive to pH, sets the pH of the reference solution 139 local to the redox species 121. In this way, in embodiments of the present disclosure, the peak potential in the voltammetric response is a constant. In some embodiments of the present disclosure, the peak potential is used by the calibration processor 150 and/or the processor 140 to calibrate the reference potential of the reference system 133. Merely, by way of example, in some embodiments, a difference between the reference potential and the peak potential may be determined and stored by at least one of the calibration processor 150 and/or the processor 140. This difference may be: measured when the electrochemical sensor 130 is initially deployed by a user using measurements from the reference system 133 and/or the calibration system; may be calculated from empirical calculations; may be determined from batch measurements made on one or more electrochemical sensors in a manufactured batch of electrochemical sensors; and/or the like.

Merely by way of example, in some embodiments, the peak potential for the redox species 121 for the set pH generated in the local environment of the reference solution 139 may be measured, calculated, determined from experiments/testing and/or the like and may be entered into the calibration processor 150 and/or the processor 140. Subsequently, when a user calibrates the reference system 133, the calibration processor 150 and/or the processor 140 may record the difference between the peak potential and the reference potential.

In operation, as described above, the reference potential of the electrochemical sensor 130 drifts as a result of changes to the reference solution 139, such as reduced concentration of chloride ions in the reference solution 139. In embodiments of the present disclosure, a voltammetric signal is repeatedly applied to the calibration system to generate a peak potential. This peak potential and the known/recorded difference between the peak potential and the reference potential, as described above, is used to process a calibration factor to calibrate any changes in the reference potential due to changes in the reference solution 139. The periodicity of the applied voltammetric signals may depend upon the use of the electrochemical sensor 130 and may be set by the calibration processor 150 and/or the processor 140, set by the user, set by the manufacturer and/or the like. For example, where the electrochemical sensor 130 comprises a glass electrode and is used for deployments of weeks/months, the periodicity may be of the order of hours or days. In sensor deployments of hours or days, the periodicity may be of the order of seconds, minutes or hours.

In embodiments of the present disclosure, by repeatedly measuring the peak potential associated with the redox species 121, the calibration system is configured to provide for online calibration of the reference potential of the reference system 133. As noted previously, the reference system 133 comprises a porous frit 137 that provides an ionicly conducting electrical pathway between the inside of the reference chamber 134 and the test solution 145. This porous frit 137 allows for dilution of the reference solution 139 and/or entry of chemical species into the reference solution 139. In tests, applicant has found that the calibration system produces a stable peak potential that is constant and dependent only upon the set pH in reference solutions less than 1 molar sodium or potassium chloride up to about 10 molar sodium or potassium chloride. This illustrates that embodiments of the present disclosure can be used in most commercially available reference systems.

Applicant has also found that the peak potential of the calibration system is stable/constant when the reference solution 139 has been diluted by up to 50%. Surprisingly, applicant has found that the peak potent of the calibration system is stable/constant when: acids, such as hydrochloric acid; bases, such as sodium hydroxide; carbonates, such as hard water; reactive chemistries, and other reactive chemistries are added to the reference solution 139. In this disclosure, reference is made to a peak potential produced by the working electrode 120 in response to an applied voltammetric signal. This peak potential corresponds to a peak/trough in the redox current produced by the redox species 121. In some embodiments, other features in the voltammetric response may be used instead of the peak potential for calibrating the reference potential. For example, rather than the peak potential the potential corresponding to another feature in the voltammetric response may be used, such as potential/position corresponding to the greatest rate of change in the response and/or the like. In embodiments of the present disclosure peak picking algorithms or the like may be used to identify a peak in the voltammetric response. In some embodiments, because the peak potential for the redox species 121 when contacted with the reference solution 139 is known/can be calculated, this known/calculated peak potential may be used to process the voltammetric response when determining the peak potential from the voltammetric response.

Figure 2B:
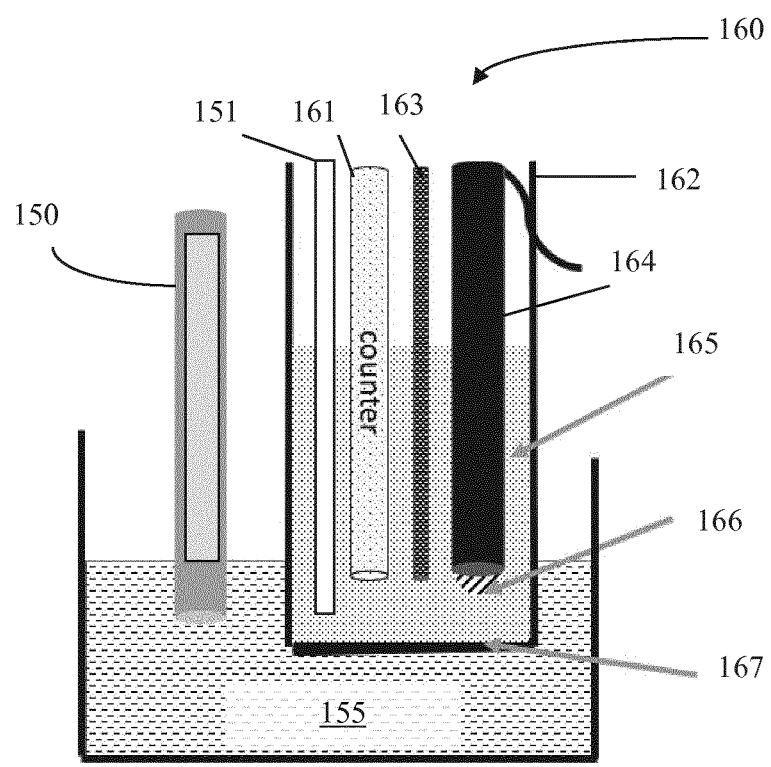
FIG. 2B illustrates an electrochemical sensor comprising a calibration system, in accordance with some embodiments of the present disclosure.

FIG. 2B illustrates an electrochemical sensor comprising a calibration system in accordance with some embodiments of the present disclosure.

The electrochemical sensor comprises a sensor electrode 150 and a reference system 160. The reference system 160 comprises a reference chamber 162 containing a reference solution 165 and a reference electrode 151. The reference electrode 151 is at least partially in contact with the reference solution 165. The reference solution 165 may comprise sodium chloride, potassium chloride etc.

The sensor electrode 150 may comprise a glass electrode, with a glass membrane etc. The sensor electrode 150 is configured to be in electrical communication/contact with a test solution 155. The reference solution 165 is configured to be in electrical communication with the test solution 155 via a porous fit 167. The reference electrode 151 is configured to generate a reference potential for the electrochemical sensor.

A typical reference electrode is the silver chloride electrode. The silver chloride reference electrode functions as a redox electrode where an equilibrium is provided between the silver metal of the reference electrode and its salt, silver chloride, of the reference solution. The reference potential is constant given the constant condition of the reference electrode and the reference solution. However, the reference potential will drift if the concentration of the silver chloride in the reference chamber changes. Since the reference solution is in fluid communication with the test solution through the porous frit 167 the concentration will change during use of the electrochemical sensor.

In embodiments of the present disclosure, a calibration electrode 163 of an additional electrochemical cell is placed inside the existing reference electrode chamber. The electrochemical cell may comprise a counter electrode 161 and an auxiliary electrode 164. In some embodiments, the reference electrode 151 may also be used as the reference electrode/auxiliary electrode 164 in the electrochemical cell. The calibration electrode 163 is the working electrode of the electrochemical cell and comprises a redox species that is immobilized on the calibration electrode 163 and both redox active, sensitive to pH, and also controls the local environment of the reference solution 165 close to the surface of the calibration electrode 163.

In some embodiments, the immobilised redox species may be solvent cast onto, electro-polymerised on, or immersed within the calibration electrode 163. The redox couple bound within the polymeric layer acts as a new stable redox couple, whilst the layers ability to control the local environment acts as a second layer to protect from any variations observed in the bulk solution in which the electrode is immersed. This additional electrochemical circuit acts as a means of correcting any drift observed in the reference electrode in-situ.

In some embodiments, the device runs under potentiometric sensing mode between the analyte sensing electrode and the reference electrode. The cell periodically runs a voltammetric sweep against the working electrode housed behind the porous frit. The potential of the redox active species immobilized on the working electrode is used to correct any drift occurring in the reference electrode. In some embodiments, the frequency of voltammetric sweep depends on the application for which the electrochemical sensor is deployed.

Figure 2C:
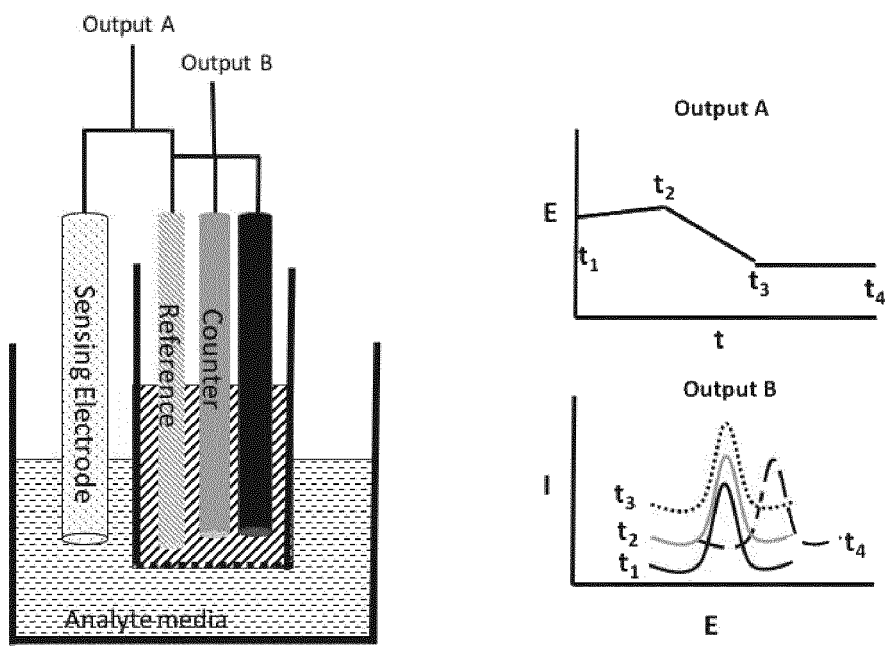
FIG. 2C depicts an electrochemical sensor comprising a calibration system, in accordance with some embodiments of the present disclosure, and outputs from the calibration system.

FIG. 2C depicts a schematic representation of a sensor output from an electrochemical sensor comprising a calibration system, in accordance with some embodiments of the present disclosure, using various voltammetric sweep profiles. In the depicted configuration, the calibration system can provide QA/QC of the sensor's reference electrode. The depicted sensor includes an integrated electrochemical cell and potentiostat, and the system uses a voltammetric signal from the potentiostat to produce a sweep between the reference electrode and the calibration electrode in the integrated electrochemical cell to generate a potential that may be used for QA/QC of the reference electrode during operation of the sensor. The sensor may in some embodiments run using a modified bi-potentiostate system. Such a set-up obviates the need for reference sensor calibration prior to deployment as is the case with current commercial ISE's. In embodiments of the present disclosure, prior to deployment, the internal circuit can be measured and this may be used to set the parameters for the reference system.

Embodiments of the present invention may use the following chemical structures on the working electrode, in which the redox active component of molecule has carboxylic, sulfonic and/or amino moieties.

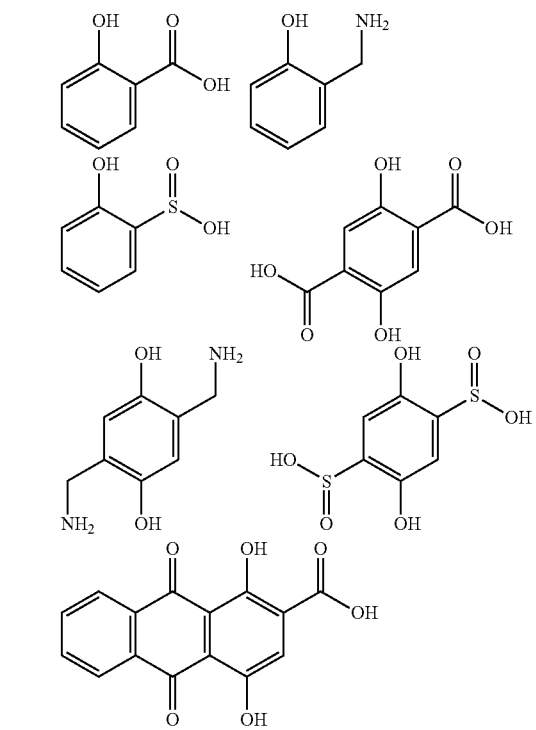

In certain cases such as that of salicylic acid (top left structure) a redox active pH active polymeric layer can be formed containing carboxylic acid moieties, which in the proposed set-up the redox active components only observes a pH of solution consistent with that of the pKa of the molecule.

In certain embodiments, the working electrode in the new electrochemical cell can have a single layer in which the redox active component has moieties attached to control the local environment directly and in other embodiments the working electrode system can have a dual layer in which the redox active components are separated/independent from the species used to control the local environment. In other embodiments, the redox active species used within the working electrode system by virtue of its oxidation or reduction can control the local environment to the surface through the release/loss or gain of protons, cations or anions.

Figure 3:
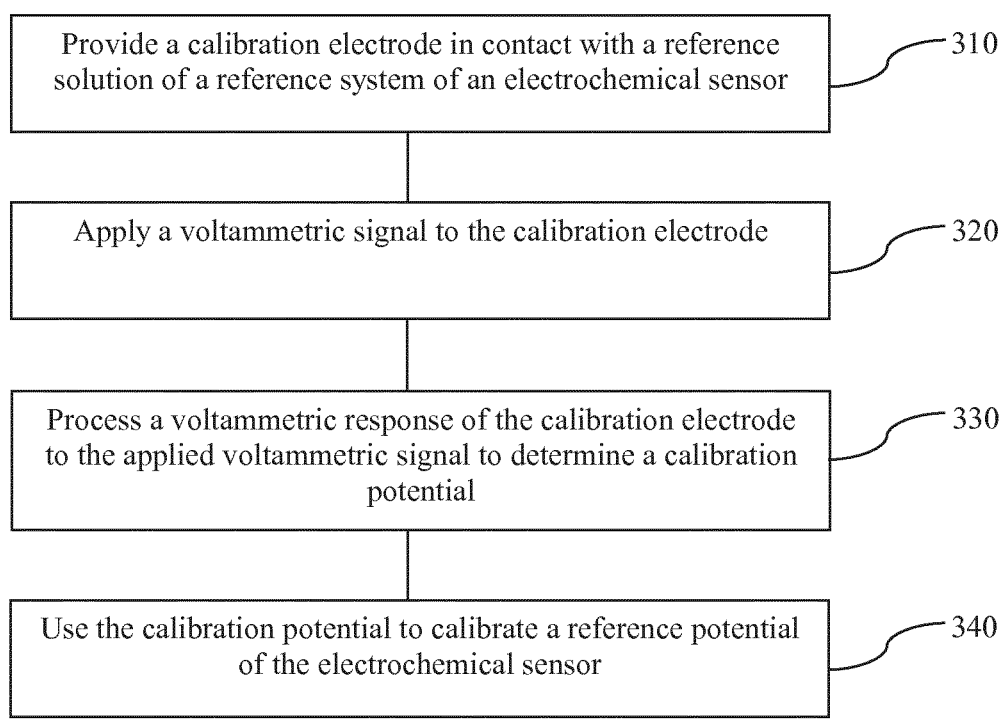
FIG. 3 is a flow-type illustration of a method for online calibration of a reference system of an electrochemical sensor, in accordance with some embodiments of the present disclosure.

FIG. 3 is a flow-type illustration of a method for online calibration of reference electrode of an electrochemical sensor, in accordance with some embodiments of the present disclosure.

In 310, a calibration electrode is provided to contact a reference solution of a reference system of an electrochemical sensor. The reference system comprises a reference chamber containing the reference solution and a reference electrode. The reference electrode may comprise a metal, carbon or the like and the reference solution may comprise a salt, such as sodium chloride, potassium chloride or the like.

The reference electrode comprises a redox active species that is sensitive to pH/proton concentration. The reference solution comprises a bufferless/low buffer capacity solution, such as potassium chloride, sodium chloride and/or the like. The redox active species is configured to set a pH of the reference solution local to/proximal to the redox active species. The redox active species may be immobilized on the calibration electrode, covalently bound to the calibration electrode and/or the like. The calibration electrode may comprise carbon, a carbon derivative, a metal, and/or the like. The redox active species is selected not to be sensitive to chloride ions/chloride ion concentration.

In 320, a voltammetric signal/a potential sweep is applied to the calibration electrode. The calibration electrode may be part of a calibration system comprising a counter electrode and the voltammetric signal may be swept between the calibration electrode, which may comprise a working electrode and the counter electrode. The voltammetric signal may comprise a potential sweep, such as a square wave, a ramped signal/wave and/or the like.

The applied voltammetric signal causes the redox active species to undergo oxidation/reduction. Since the redox active species is sensitive to pH/proton concentration of the reference solution it is in contact with, the oxidation/reduction current will be determined by the pH of the reference solution. Moreover, because the reference solution is a bufferless/low buffer solution, the pH of the reference solution proximal to the redox species is set by the properties of the redox active species. In some embodiments, the redox active species may comprise an acid, a base, acid moieties, basic moieties and/or the like. In other embodiments, the redox active species may trigger the pH of the local environment by donating or consuming protons when an electrochemical/voltammetric signal/potential sweep is applied to the redox active species. For example, in some embodiments, the redox active species may comprise anthraquinone and the anthraquinone may set the local pH of the reference solution to a pH of approximately 10 by consuming protons. Because the redox active species is selected to set the pH of the reference solution local to the redox active species, the peak potential of the reduction/oxidation current will be determined by the pH set by the redox active species.

In 330, a voltammetric response of the calibration electrode to the applied voltammetric signal is processed to determine a calibration potential. In some embodiments, the calibration potential is the peak potential produced by the redox active species in response to the applied voltammetric signal. In some embodiments, the voltammetric response may be a current versus potential and the voltammetric response may contain a peak/singularity corresponding to a peak/trough in the redox current of the redox active species. The potential corresponding to this peak/singularity in the redox current is the peak potential. In some embodiments, other features of the peak/singularity may be used as a calibration potential. Because the redox current and the peak potential for the redox active species correspond to the pH of reference solution seen by the redox active species, and because the redox active species sets the pH of the reference solution local to the redox active species, the redox current and the peak potential are a constant. In embodiments of the present disclosure, the redox active species is selected such that its redox response is not affected by chloride concentration in the reference solution. This and the fact that applicant has found that the response of the redox active species in the present arrangement is not sensitive to acids, basis, hard water, reactive chemistries and/or the like in the reference solution means that the calibration electrode provides a constant/stable response to the applied voltammetric signal over a wide range of challenging chemical applications.

In 340, the calibration potential is used to calibrate the reference potential of the electrochemical sensor. In some embodiments, a determined difference between the calibration potential and the reference potential is used for online calibration of the electrochemical sensor. For example, the reference potential of the electrochemical sensor may be determined when the sensor is new, being deployed, being calibrated and/or the like. At this time, a difference between the reference potential and the calibration potential may be determined and stored. The calibration potential itself may be calculated, measured, determined from experimentation, be measured during manufacture of the electrochemical sensor and/or the like. In operation when the electrochemical sensor is being used, a periodic measurement of the calibration potential is processed and compared to the reference potential. If the difference between the calibration potential and the reference potential has changed with respect to the stored difference, the reference potential is recalibrated to account for this change. In this manner, the reference potential for the electrochemical sensor can be recalibrated online, while the electrochemical sensor is deployed and making measurements.

Polymer Layer

Figure 4:
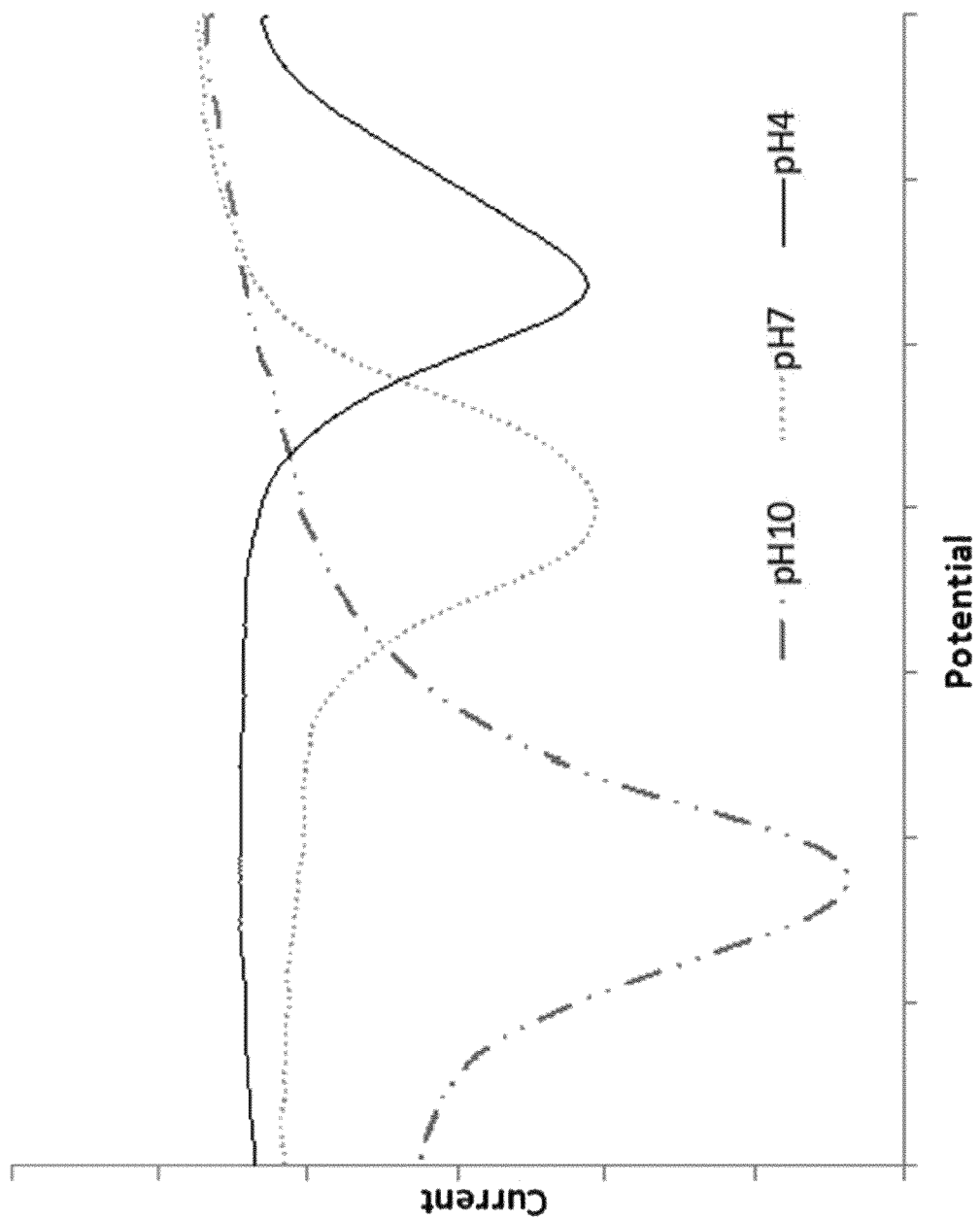
FIG. 4 is a graph that displays the response of AQ modified electrodes in pH 4, 7 and 10 buffers

Rigorous testing of the redox active component in the presence of a number of different anions and cations showed an independence of the peak potential with ion concentration and charge. However, due to the nature of the reference system—controlling the local environment through perturbing the pH of the solution—in media of high buffer concentration, the measurement proves problematic as the local environment is swamped by the buffer and hence the local pH will be that of the bulk solution. Therefore rather than acting as a reference compound, the redox active species will have a redox potential dependent on the pH of the bulk solution. FIG. 4 details an AQ electrode in three IUPAC buffered media; pH 4 phthalate, pH 7 phosphate and pH 10 carbonate buffer. It is evident that under these conditions the AQ modified electrode no longer acts as a reference system. It is thus desired to minimize this pH shift behaviour seen in highly buffered media.

The use of polymeric layers in electrochemical sensors to increase lifetimes or to increase selectivity for specific analytes through either molecular (host/guest) or charge (anion/cation) interactions is well known. Examples of these systems are vanillomycin used to preferentially determine potassium over calcium, or anionic films (Nafion) to selectively retard a number of biological redox active interferences (ascorbic acid, uric acid etc . . . )

In the proposed invention, the use of polymeric layers to impart further control on the local environment is proposed. The polymeric layer provides a constrained environment in which the electrochemistry can occur and within a hindered diffusion regime to the bulk solution. This will minimise the effect of the bulk solution on the local environment perturbation, and thus allows greater control over the local environment.

Figure 5A:
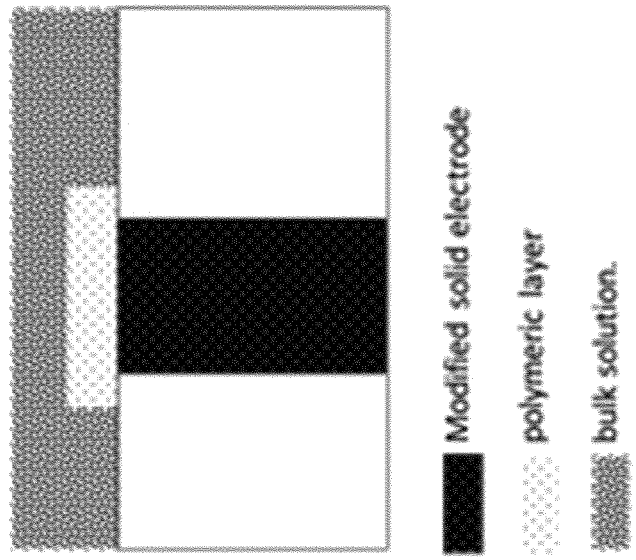
FIG. 5A shows a four component system incorporating the solid electrode, the electroactive system, the polymeric layer and the bulk solution.
Figure 5B:
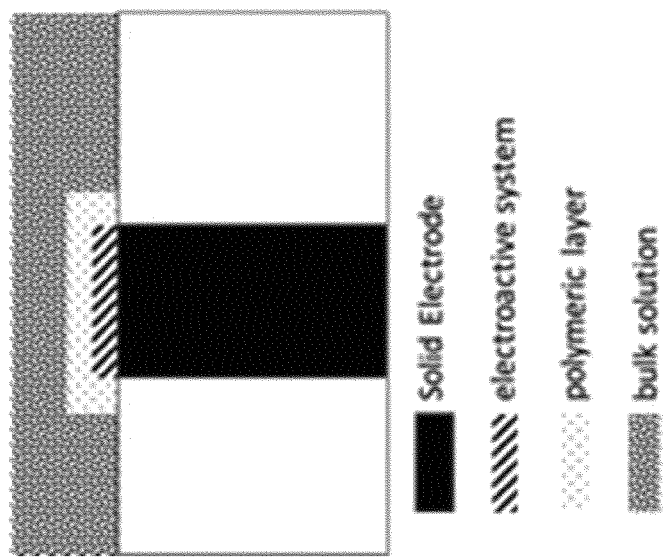
FIG. 5B shows a three component system comprising of the solid electrode in which the electroactive species is immobilized, a polymeric layer and the bulk solution.

FIG. 5 details two types of electrode set-ups. FIG. 5A incorporates four components; the electrode, the electroactive system, the polymeric layer and the bulk solution. In this set-up the electroactive species is either chemically or physically immobilized onto the surface of the electrode, and the polymer is then immobilised upon the surface. In such instance the polymer can be immobilised onto the electrode surface through solvent casting, or electrochemical or chemically polymerized onto the surface in-situ. The fourth component is the bulk solution. FIG. 5B details a three component system involving a bulk modified electrode, a polymeric layer and the bulk solution. In this case the conducting electrode contains the redox moiety within the bulk of the electrode. The polymer is immobilised on the electrode surface through solvent casting or electrochemical or chemically polymerization onto the surface in-situ. It should be noted that in certain embodiments, one or more polymeric layers can be placed onto the electroactive surface, to provide further control of the surface.

In certain cases the polymer can be anionically charged (Nafion, anionic polyacrylamides, salicylic acids), cationically charged (e.g., polylysine, polyornithine, polybrene, polyethyleneimine, cyclodextrin, chitosan, histone, collagen) or neutral (polyacrylamides, polyacrylates, polysaccharides, polysulfone, polyaniline, polythiophene etc . . . ) depending on the pH of the bulk solution.

It should be noted that the charge of the polymer may be dependent upon the bulk solution which the polymer is in. For example, Polyaniline may be naturally charged in a low pH solution, whilst being neutral at higher pH solution. A further example is that Nafion may be neutral when in a solution below a pH of approximately 2 whilst being anionically charged when in a solution above a pH of approximately 2.

Figure 6:
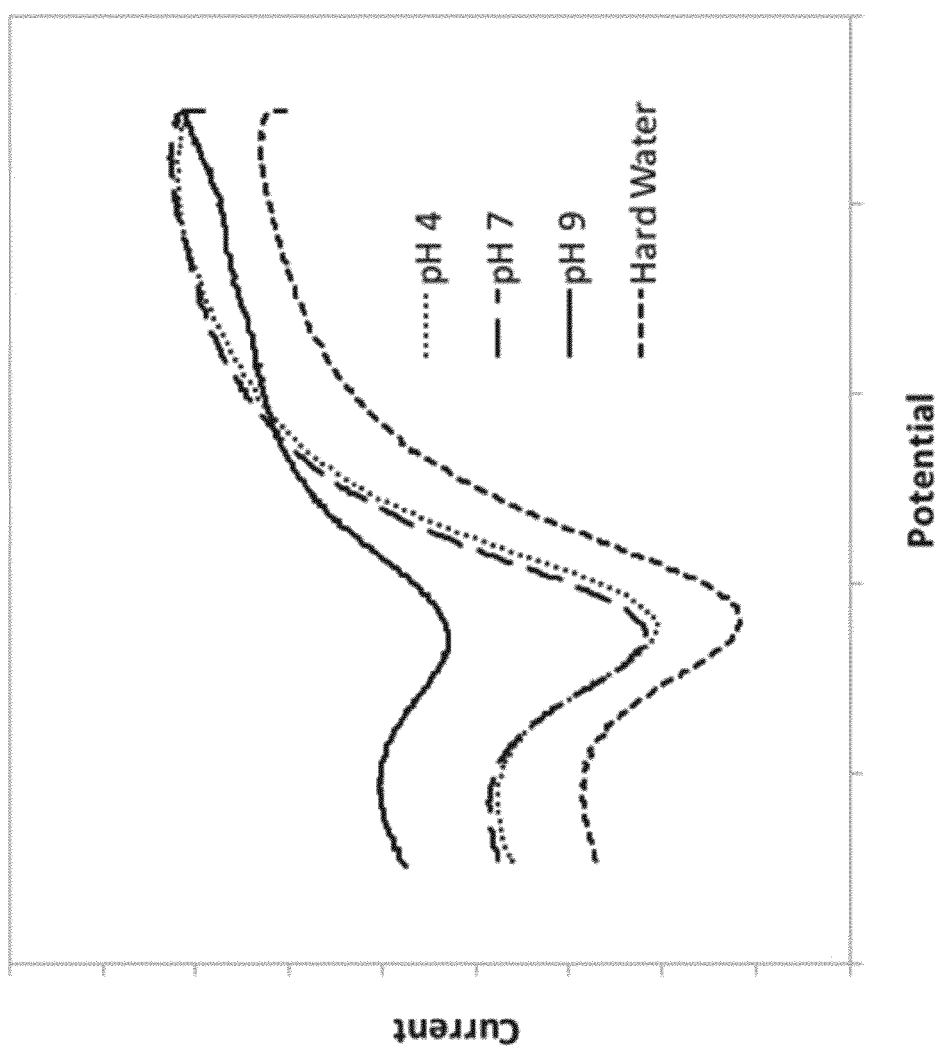
FIG. 6 is a graph that displays the Electrochemical response of Nafion coated system in pH 4, 7 and 10 buffers.

FIG. 6 details the electrochemical system shown to be pH responsive in buffered media (FIG. 4) with a Nafion coating, when placed in 3M KCl, pH 4, pH 7, pH 10 buffers and a hard water sample with 1M KCl present. It can be clearly seen that unlike the data presented in FIG. 4, the peak potential is now independent of pH of the sample, showing that the nafion layer imparts further control on the environment local to the electrode surface. The pH of the surface in this case is set by the uptake of protons local to the electrode surface due to the reduction of the anthraquinone moiety.

Figures 7A, 7B, 7C:
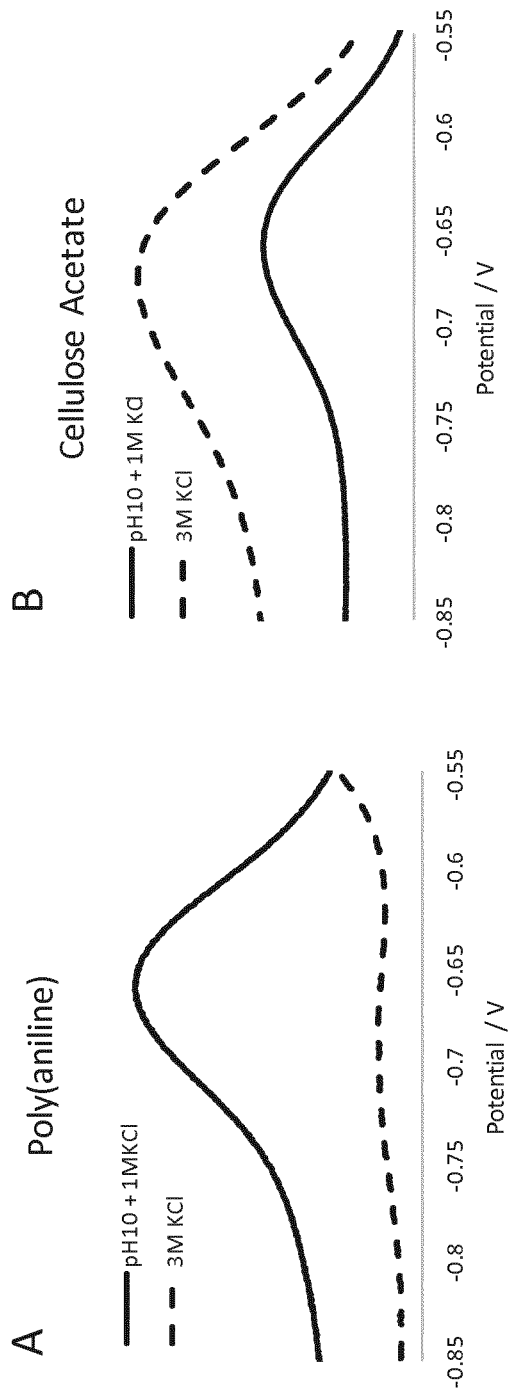
FIG. 7 details the response of a) polyaniline, b) cellulose acetate and c) an electropolymerised salicylic acid coated electrode when placed in 3M KCl and pH 10 solution.

FIG. 7 details the response of a) polyaniline, b) cellulose acetate and c) an electropolymerised salicylic acid coated electrode when placed in 3M KCl and pH 10 solution. Minimal shift is observed between the buffered and unbuffered responses, showing the efficacy of using these layers to provide stability on the peak potential in the various media. In these systems, both polyaniline and cellulose acetate will have a neutral charge, whilst the electropolymerised salicylic acid will have an anionic charge.

Multiple Cycles and Time Between Scans

To understand how the polymeric layer imparts stability on the electrode layer, various experiments were conducted to understand how the imposition of electrode potential effects the equilibrium of the system. To achieve this a Nafion coated electrode was placed in a pH 10 buffered solution and the potential was cycled 20 times continuously with no delay between scans. The electrode was then left under quiescent conditions for a known period prior to the potential being cycled again. This process was then repeated. FIG. 8 details the plot of peak potential against time showing the peak potential measured for the first, 10th, 15th and 20th scan. It can be seen that repetitively scanning the potential shifts the peak potential to a lower value. Furthermore, the data shows when a short time period is left between the consecutive scans (ca. 2-50 mins, FIG. 8A) the peak potential observed on the first scan does not return to the peak potential observed on scan 1 at 0 minutes. However, when a longer time period is left between the scans (80 mins, FIG. 8B), the peak potential measured on the first scan returns to the starting potential, indicating the system has returned to equilibrium. The data can be explained as, following the first 20 initiation scans, the potential is lowered due to the electrochemical process consuming protons at the electrode surface, after each scan the local pH becomes more alkaline as further protons are consumed. The polymeric layer hinders the rate of proton transfer from the bulk solution to the electrode surface, and as such the equilibrium between the bulk and electrode surface cannot be maintained. The local environment pH is then controlled by the consumption of protons at the electrode surface. Under quiescent conditions, for short periods of time, the local pH is still not consistent with the bulk pH, as diffusion is slow to the electrode surface through the polymeric layer and hence the peak potential is lower than at scan 1 time 0. Only after a significant period of time between scans (ca. 80 mins) does equilibrium between the local environment and the bulk solution return.

While the principles of the disclosure have been described above in connection with specific apparatuses and methods, it is to be clearly understood that this description is made only by way of example and not as limitation on the scope of the invention.

What is claimed is:

1. An online calibration system for an electrochemical sensor, comprising:
a calibration electrode in a reference solution, the calibration electrode comprising:
a redox species, wherein:
the redox species is configured to set a pH of the reference solution in a local environment proximal to the calibration electrode;
the redox species is configured to undergo oxidation and/or reduction when an electrochemical signal is applied to the calibration electrode; and
the redox species is sensitive to pH and generates a response to the applied electrochemical signal that is dependent on the pH of the local environment proximal to the calibration electrode, and
a polymeric layer positioned between the redox species and the reference solution.

2. The online calibration system according to claim 1, wherein the polymeric layer is anionically charged.

3. The online calibration system according to claim 1, wherein the polymeric layer is formed of Nafion and/or anionic polyacrylamides and/or salicylic acid.

4. The online calibration system according to claim 1, wherein the polymeric layer is cationically charged.

5. The online calibration system according to claim 1, wherein the polymeric layer is formed of polylysine and/or poly ornithine and/or polybrene and/or polyethyleneimine and/or cyclodextrin and/or chitosan and/or histone and/or collagen.

6. The online calibration system according to claim 1, wherein the polymeric layer is neutral.

7. The online calibration system according to claim 1, wherein the polymeric layer is polyacrylamides and/or polyacrylates and/or polysaccharides and/or polysulfone and/or polyaniline and/or polythiophene.

8. The online calibration system according to claim 1, wherein the redox species is chemically or physically immobilized on a surface of the calibration electrode.

9. The online calibration system according to claim 8, wherein a polymer of the polymeric layer is immobilised over the redox species.

10. The online calibration system according to claim 1, wherein the calibration electrode contains the redox species in a bulk of the calibration electrode.

11. The online calibration system according to claim 10, wherein the calibration electrode contains the redox species throughout an entire structure of the calibration electrode.

12. The online calibration system according to claim 1, wherein a polymer of the polymeric layer is immobilised onto the surface of the calibration electrode.

13. The online calibration system according to claim 12, wherein the polymer is immobilised through solvent casting or electrochemical polymerization or chemical polymerization.

14. The online calibration system according to claim 1, wherein the redox species is configured to consume or donate protons when the electrochemical signal is applied to the calibration electrode.

15. The online calibration system according to claim 1, wherein the electrochemical signal comprises a potential sweep and/or a voltammetric signal.

16. The online calibration system according to claim 14, wherein the redox species comprises anthraquinone or a derivative thereof.

17. The online calibration system according to claim 1, wherein the reference solution comprises sodium chloride or potassium chloride.

18. The online calibration system according to claim 1, further comprising:
a processor in communication with the calibration electrode and a reference electrode of the electrochemical sensor and configured to use the electrochemical response to calibrate a reference potential of the reference electrode.

19. The online calibration system according to claim 18, wherein the electrochemical response comprises a peak potential corresponding to a maximum of an oxidation current or a minimum of a reduction current produced by the redox species.

20. The online calibration system according to claim 1, further comprising:
a potentiostat configured to generate the electrochemical signal.

21. The online calibration system according to claim 1, wherein the electrochemical signal comprises one of a square wave, a ramped wave and/or a pulsed wave.

22. The online calibration system according to claim 1, further comprising:
either separate counter and reference electrodes and/or a combined counter-reference electrode.

23. The online calibration system according to claim 22, wherein the electrochemical signal is applied between the calibration electrode and either the separate counter and reference electrodes and/or the combined counter-reference electrode.

24. The online calibration system according to claim 1, wherein the calibration electrode comprises at least one of a microelectrode and a microelectrode array.

25. The online calibration system according to claim 1, wherein the calibration electrode and the reference solution are disposed within a reference cell of the electrochemical sensor.

26. The online calibration system according to claim 25, wherein the reference cell comprises a frit configured to contact a fluid being sensed by the electrochemical sensor.

27. An electrochemical sensor comprising the calibration system according to claim 1.

28. The electrochemical sensor of claim 27, wherein the electrochemical sensor comprises one of a glass electrode, an ISFET or a potentiometric sensor for measuring concentration or presence of a specific ion.

29. A method for online calibration of an electrochemical sensor, the method comprising:
placing a calibration electrode in a reference solution of the electrochemical sensor, wherein the calibration electrode comprises a redox species configured to control pH of a local environment proximal to the electrode and a polymeric layer positioned between the redox species and the reference solution;
applying a voltammetric signal to the calibration electrode to produce oxidation and/or reduction of the redox species; and
using a calibration potential corresponding to a feature of an oxidation or a reduction current generated by the redox species to calibrate a reference potential of the electrochemical sensor.

30. The method according to claim 29, wherein using the calibration potential to calibrate the electrochemical sensor comprises using a difference between the reference potential of a reference electrode and the calibration potential to calibrate the reference potential.

31. The method according to any one of claim 29, wherein applying a voltammetric signal to the calibration electrode comprises applying a voltammetric sweep across the calibration electrode and a calibration reference electrode.

32. The method according to claim 31, wherein the calibration reference electrode comprises a reference electrode of a potentiometric sensor.

33. The method according to any one of claim 32, wherein the potentiometric sensor is calibrated at the same time as it is being used to sense properties of fluid.

34. The method according to claim 29, wherein the reference solution is contained in a reference cell of the electrochemical sensor.

35. The method according to claim 29, wherein the voltammetric signal is applied periodically to the calibration electrode.

36. The method according to claim 29, wherein the redox species is configured to set the pH of the local environment to a pH value less than 6 or a pH value greater than 8.

37. The method according to claim 29, wherein the reference solution comprises one of: potassium chloride and sodium chloride.

38. The method according to claim 29, wherein the voltammetric signal is applied multiple times prior to using the calibration potential to calibrate a reference potential of the electrochemical sensor.

39. The method according to claim 38, wherein the voltammetric signal is applied at least 20 times prior to using the calibration potential to calibrate a reference potential of the electrochemical sensor.

40. The method according to claim 38, wherein the voltammetric signal is applied 5 or 10 or 15 or 20 times prior to using the calibration potential to calibrate a reference potential of the electrochemical sensor.

41. The method according to any one of claim 29, wherein a wait time is established between the applying of the voltammetric signal and the application of a next voltammetric signal.

42. The method according to claim 41, wherein the wait time is 50 minutes or more.

43. The method according to claim 42, wherein the wait time is 80 minutes or more.

* * * * *